United States Patent [19]

Fry

[11] Plant 4,771

[45] Sep. 29, 1981

[54] MUSCADINE GRAPE

[76] Inventor: Byard O. Fry, 612 Terrace St., Griffin, Ga. 30223

[21] Appl. No.: 795,116

[22] Filed: May 9, 1977

[51] Int. Cl.[3] ..... A01H 5/03
[52] U.S. Cl. ..... Plt./47
[58] Field of Search ..... Plt./47

*Primary Examiner*—Robert E. Bagwill

*Attorney, Agent, or Firm*—Stanley L. Tate

[57] ABSTRACT

A new variety of Muscadine which is very vigorous, with large fruit of a russetted light bronze color, which occurs in medium clusters of from four to eight berries, each berry having a diameter of about 1-3/16 inches, an individual berry sugar content of from about 18.5 to 21.3 percent and producing a fruit yield of from $3\frac{1}{2}$ to $4\frac{1}{2}$ tons per acre.

1 Drawing Figure

DESCRIPTION OF THE VARIETY

The new and distinct variety of muscadine grape which is the subject of the present application was originated by crossing the unnamed pollen parent seedling 29-49 with a female parent of the Fry Variety.

The general objective of this breeding was to produce an improved variety of self pollenating large fruited muscadine plant with individual berries having a similar size to the berries of the female parent, which berries appear in a loose cluster thereby protecting the berries from disease and insect damage. The new and distinct variety of muscadine, herein described and claimed, meets all of the aforesaid requirements, all of which distinguish it from its parents, as well as from all other varieties of muscadine of which the applicant is aware.

In comparison, with both the seed and pollen parents, the new variety produces fruit much larger than the small fruited pollen parent and similar in size to that of the seed parent. The fruit of the pollen parent usually has an average berry diameter of 0.75 inches and the fruit of the new variety and the seed parent usually has an average berry diameter of about 1-3/16 inches. The fruit of the present variety contains an average of from about 18.5 to 21.3 percent soluble sugar which is a higher sugar content than that of the pollen parent but similar to the sugar content of the seed parent. Further, the present variety yields on the average from three and one-half ($3\frac{1}{2}$) to four and one-half ($4\frac{1}{2}$) tons of fruit per acre.

Asexual reproduction of the new variety by layering or cuttings as performed at Brooks, Ga., shows that the foregoing characteristics and distinctions come true to form and are established and transmitted through succeeding propagations.

The accompanying photograph shows a typical specimen of the vegetative growth and fruit of the new variety where the fruit is ripe and ready for picking and as depicted in color as nearly true as it is reasonably possible to make the same in color illustration of this character.

The following is a detailed description of the new variety.

Species: *Vitis rotundifolia.*
Type: Vine.

Seed parent: Fry variety.
Pollen parent: Seedling 29-49.
Propagation: Holds its distinguishing characteristics through succeeding propagations by layering and cuttings.
Locality where grown and observed: Brooks, Ga.
Fruit borne: Usually in medium clusters of from 4 to 8 berries.
Fruit size: Very large, similar in size to the seed parent; about 1-3/16 inches in diameter.
Fruit color: Light bronze, some russetting.
Fruit maturity: September 15 to October 15 at Brooks, Ga., depending upon seasonal conditions.
Fruit shape: Uniform round.
Sugar content: Individual berries from about 18.5 to 21.3 percent.
Seeds:
*Average diameter.*—5/32 inches.
*Average seeds per berry.*—3.10.
Pulp:
*Color.*—Fan 2-195B.
*Consistency.*—Soft and juicy.
Skin color: Fan 4-160C.
Leaf color: Fan 3-136B.
Reproductive organs: Self-pollenating.
Growth: Very vigorous.
*Habit.*—Vine, requires support.
*Canes.*—Heavy caliper.
Disease resistance: Very good resistance to bitter and soft rot and to insect damage. Leaves are tolerant to black rot.

This description was made from a muscadine vine of the new variety bearing ripe fruit in mid September at Brooks, Ga. All color designations used herein refer to the color designations of The Royal Horticultural Society, London, England, color chart.

What is claimed is:

1. The new and distinct hybrid plant variety of muscadine as described and illustrated which is primarily distinguished as to novelty by the unique combination of very large fruit having a diameter of about 1-3/16 inches, said fruit occurring in medium clusters of from 4 to 8 berries, an individual berry sugar content of from about 18.5 to 21.3 percent and producing a crop yield of from about $3\frac{1}{2}$ to about $4\frac{1}{2}$ tons per acre.

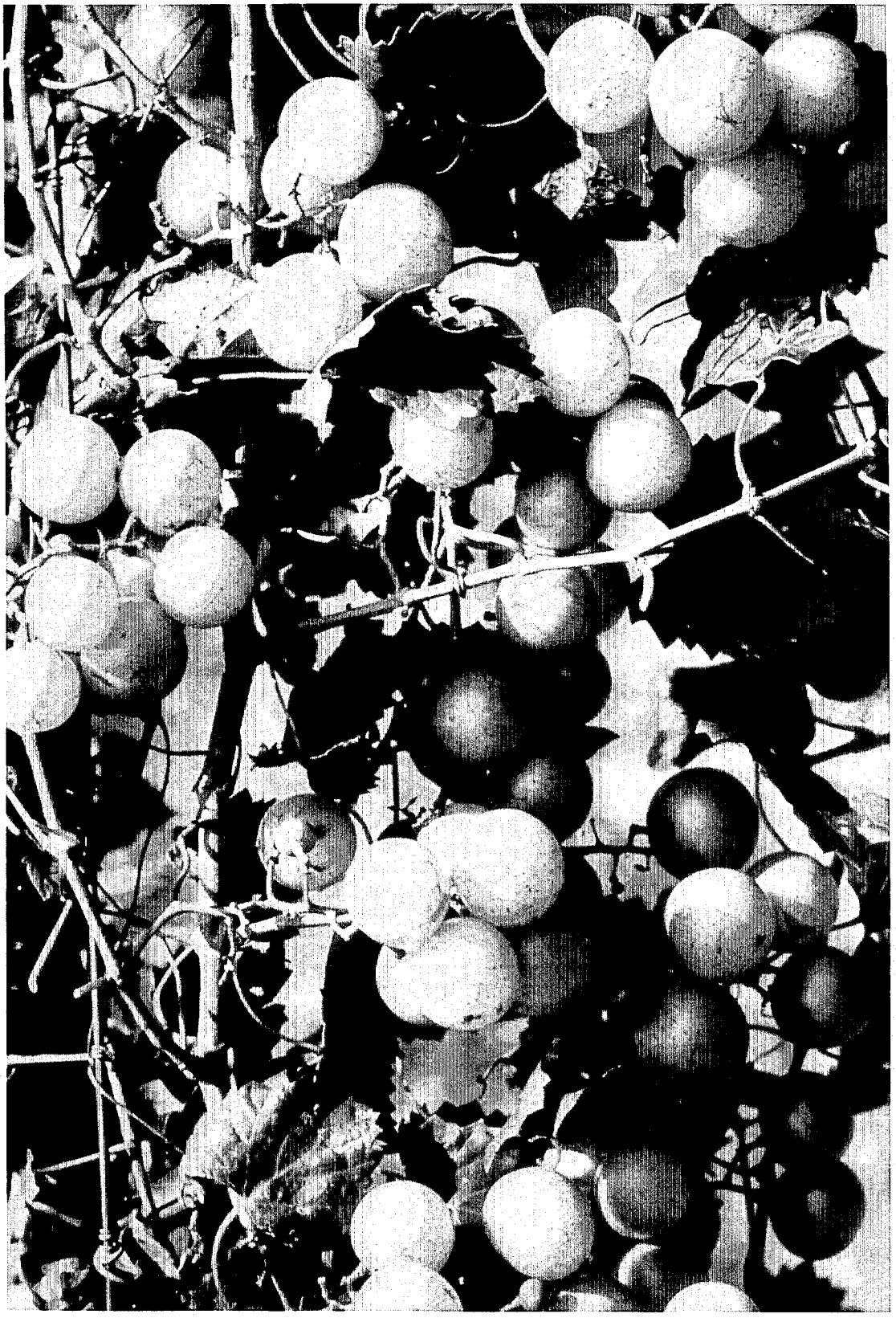

* * * * *